US009820773B2

(12) United States Patent
Lieser et al.

(10) Patent No.: US 9,820,773 B2
(45) Date of Patent: Nov. 21, 2017

(54) EMERGENCY FOREIGN OBJECT EXTRACTING DEVICE FOR CHOKING VICTIMS

(71) Applicants: Steven James Lieser, Eureka, MO (US); Christine Lieser, Eureka, MO (US)

(72) Inventors: Steven James Lieser, Eureka, MO (US); Christine Lieser, Eureka, MO (US)

( * ) Notice: Subject to any disclaimer, the term of this patent is extended or adjusted under 35 U.S.C. 154(b) by 0 days.

(21) Appl. No.: 15/050,771

(22) Filed: Feb. 23, 2016

(65) Prior Publication Data

US 2016/0249950 A1 Sep. 1, 2016

Related U.S. Application Data

(60) Provisional application No. 62/121,781, filed on Feb. 27, 2015.

(51) Int. Cl.
| | | |
|---|---|---|
| *A61B 17/50* | (2006.01) | |
| *A61M 16/00* | (2006.01) | |
| *A61M 16/04* | (2006.01) | |
| *A61M 1/00* | (2006.01) | |
| A61B 17/24 | (2006.01) | |
| A61M 16/10 | (2006.01) | |

(52) U.S. Cl.
CPC .......... *A61B 17/50* (2013.01); *A61M 1/008* (2013.01); *A61M 16/0048* (2013.01); *A61M 16/049* (2014.02); *A61B 17/24* (2013.01); *A61M 16/105* (2013.01); *A61M 2205/076* (2013.01)

(58) Field of Classification Search
CPC ............ A61M 16/0048; A61M 16/047; A61M 16/0463; A61M 1/008; A61M 16/049; A61B 17/50; A61B 17/12104; A61D 1/12
See application file for complete search history.

(56) References Cited

U.S. PATENT DOCUMENTS

| 3,175,557 A | * | 3/1965 | Hammond | ............ | A61M 1/008 |
| | | | | | 128/207.14 |
| 4,662,367 A | * | 5/1987 | Gore, Jr. | ................ | A61B 17/24 |
| | | | | | 128/202.28 |

(Continued)

OTHER PUBLICATIONS

Accessories Morgan Scientific, Pulmonary Function Test Equipment and PFT Software http://morgansci.com/pft-test-equipment-Software/accessories (Last accessed Apr. 11, 2016).

(Continued)

*Primary Examiner* — Thomas McEvoy
(74) *Attorney, Agent, or Firm* — Kutak Rock LLP; Sara Weilert Gillette

(57) ABSTRACT

A rescue device for a choking victim and a method of rescuing a choking victim is provided. The device includes a first tube that is configured to be inserted into the victim's mouth so as to assist in dislodging a foreign object in the victim's windpipe by creating a low-pressure environment within the victim's mouth. The device further includes a second tube that is configured to allow a rescuer to create the low-pressure environment in the victim's mouth by sucking on a second tube of the device. A filter is positioned between the first and second tubes to reduce sanitary concerns and to prevent the foreign object from becoming lodged in the rescuer's windpipe.

4 Claims, 2 Drawing Sheets

(56) References Cited

U.S. PATENT DOCUMENTS

| | | | | |
|---|---|---|---|---|
| 4,685,472 | A | * | 8/1987 | Muto ............... A61M 1/0056 210/446 |
| 4,813,931 | A | * | 3/1989 | Hauze ............... A61M 1/0001 600/573 |
| 4,947,841 | A | * | 8/1990 | Ng ............... A61M 1/0001 128/207.14 |
| 2002/0031559 | A1 | * | 3/2002 | Liang ............... A61K 9/02 424/725 |
| 2007/0113843 | A1 | * | 5/2007 | Hughes ............ A61M 16/0057 128/200.24 |
| 2009/0228018 | A1 | * | 9/2009 | Winiarski ............ A61M 16/06 606/106 |
| 2017/0065789 | A1 | * | 3/2017 | Reed ............... A61M 16/0833 |

OTHER PUBLICATIONS

Medicomp Bacterial Filtration Efficiency Filters & Viral Filtration Efficiency Filters http://www.mediocompmedical.com/bacterial-viral-filters.html (Last accessed Apr. 11, 2016).

http://www.morgansci.com/pft-test-equipment-software/morgan-heated-fvl-pneumotachograph/ (Last accessed May 27, 2016).

* cited by examiner

EMERGENCY FOREIGN OBJECT EXTRACTING DEVICE FOR CHOKING VICTIMS

CROSS-REFERENCE TO RELATED APPLICATIONS

This application claims priority pursuant to 35 U.S.C. 119(e) to U.S. Provisional Patent Application Ser. No. 62/121,781, filed Feb. 27, 2015, the entire disclosure of which is incorporated herein by reference.

FIELD OF THE INVENTION

The present invention relates generally to emergency devices. More specifically, the present invention is concerned with an emergency device for and method of extracting a foreign object from a choking victim.

BACKGROUND

Annually, approximately 112,500 children under the age of 14 are hospitalized with foreign objects lodged in their windpipe. These foreign objects can prevent or otherwise impede airflow, causing oxygen deprivation which can lead to brain damage and even death. The longer the airflow is impeded, the more severe the brain damage can be and the higher the risk of death becomes. Some methods of removing foreign objects include the Heimlich maneuver and swiping a finger across the back of the victim's throat. Unfortunately, the Heimlich maneuver can break the victim's ribs and swiping a finger across the back of a victim's throat can cause the object to become further lodged within the victim's windpipe. Consequently, it would be beneficial to have a device for and a method of extracting foreign objects from a victim's windpipe that would not risk breaking the victim's ribs and would not cause the foreign object to become further lodged in the victim's throat. Furthermore, few people are properly trained to perform these procedures and therefore are reluctant to attempt such procedures when the need for such procedures arises. Consequently, it would be beneficial if the device was simple to use and the method was easy to perform so that an average person would be capable of, and willing to, utilize the device and the method in an emergency situation.

Some rescue procedures, such as traditional mouth to mouth resuscitation, require the rescuer to be exposed to the victim's bodily fluids. Because such contact is socially awkward and can cause the spread of disease, some potential rescuers will hesitate or refuse to perform the rescue procedure. Even when such hesitations do not exist, some potential methods of helping a victim place the rescuer at too great of risk for the method to be a viable method. For instance, sucking a foreign object from a choking victim's windpipe creates the risk that the foreign object will become lodged in the rescuer's windpipe. Consequently, it would be beneficial for a potential rescuer to have a device for and a method of safely and sanitarily sucking a foreign object from a victim's windpipe.

While choking hazards are most frequently associated with young children, teenagers and adults are not immune from such hazards. Consequently, it would be beneficial if the device for removing a foreign object from a victim's windpipe could be used with victims regardless of their age or size.

SUMMARY

The present invention comprises a rescue device that is configured to allow a rescuer to quickly, easily, and sanitarily assist a choking victim. The device includes a first tube that is configured to be inserted into the victim's mouth so as to enable the rescuer to create a low-pressure environment within the victim's windpipe, thereby assisting in dislodging a foreign object from the victim's windpipe. The device further includes a means for and method of quickly and easily creating the low-pressure environment. In some embodiments, the means includes a second tube and the method includes sucking on the second tube by the rescuer.

In a preferred embodiment, the device includes a filter. In some embodiments, the filter improves sanitation of the procedure. In other embodiments, the filter prevents the foreign object from traveling into the rescuer's mouth, thereby preventing the rescuer from becoming a choking victim.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION OF A PREFERRED EMBODIMENT

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
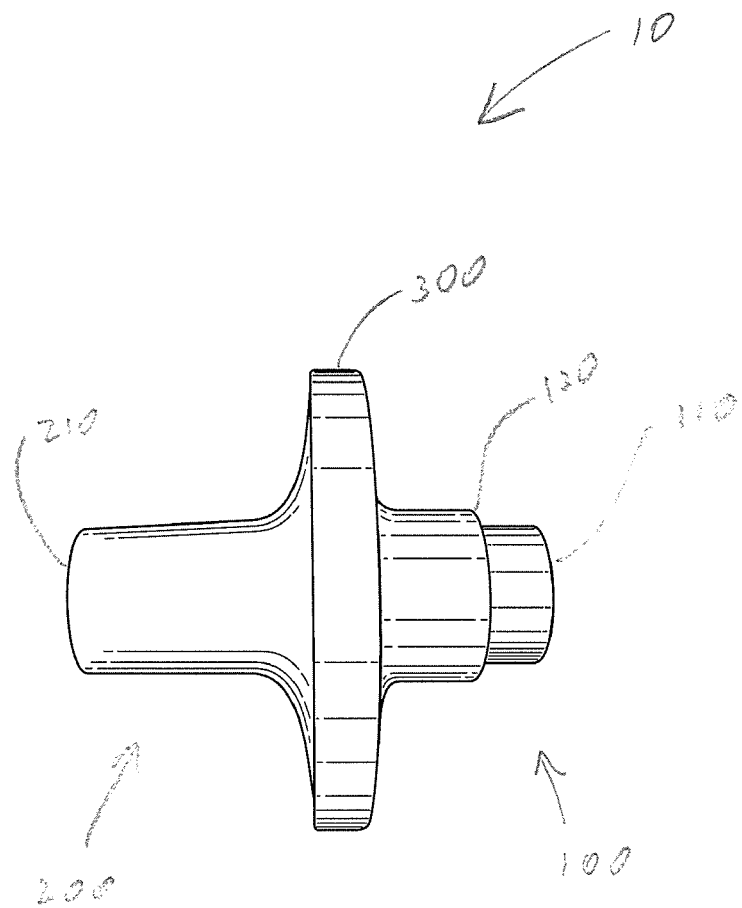
FIG. 1 is a side view of the present invention.
Figure 2:
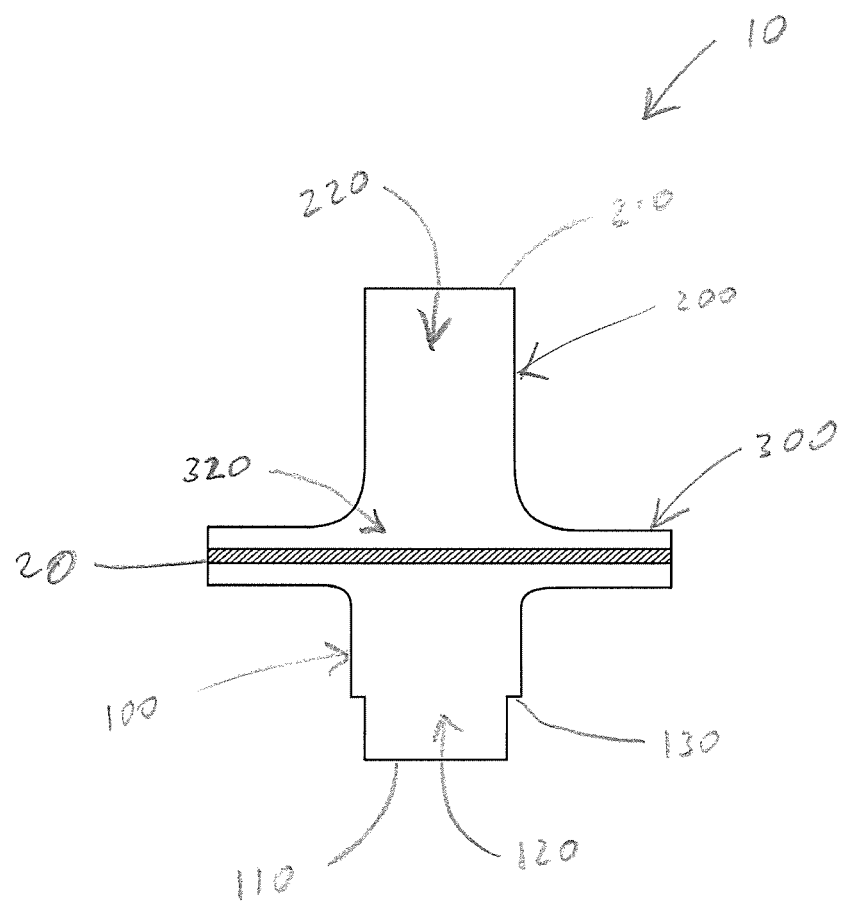
FIG. 2 is a section cut of the present invention.

Referring to FIGS. 1 and 2, a preferred embodiment of the present invention includes a main body 300 defining an interior area 320 and a first tube 100 extending from a first end of the main body. In some embodiments, the first tube 100 defines a first opening 110 and a first passageway 120 extending between the first opening 110 and the interior area 320 of the main body 300. In this way, objects and/or gas, such as air, entering the first tube 100 through the first opening 110 are able to move into the interior area 320 of the main body 300.

In a preferred embodiment, the first tube 100 comprises a continuous outer wall extending from the main body 300 to the first opening 110. In some embodiments, the continuous outer wall is shaped and sized so as to be capable of being inserted into a mouth of a choking victim. In some such embodiments, the continuous outer wall is generally cylindrical.

In some embodiments, the continuous outer wall defines a first diameter adjacent to the first opening 110. In some such embodiments, the first diameter is approximately between three-fourths and one and one-half of an inch. In other such embodiments, the continuous outer wall comprises a step 130 that is displaced from the first opening 110 such that the continuous outer wall also defines a second diameter adjacent to the step 130. In some such embodiments, the first diameter is smaller than the second diameter with the first diameter being generally sized for use with children and the second diameter being generally sized for use with adults.

In some embodiments, a longitudinal axis of the first tube 100 extends from the first opening 110 to the interior area 320 of the main body 300. In some such embodiments, a cross section of the first passageway 120 adjacent to the first opening 110 and perpendicular to the longitudinal axis of the first tube 100 defines a first area. In other such embodiments, a cross section of the first passageway 120 adjacent to the step 130 and perpendicular to the longitudinal axis of the first tube 100 defines a second area. In some such embodiments, the second area is larger than the first area.

In a preferred embodiment, a second tube 200 extends from a second end of the main body 300. In some embodiments, the second tube 200 defines a second opening 210 and a second passageway 220 extending between the second opening 210 and the interior area 320 of the main body 300. In this way, fluid, such as air, in the interior area 320 of the main body 300 are capable of being withdrawn from the interior area 320 through the second passageway 220.

In a preferred embodiment, the second tube 200 comprises a continuous outer wall extending from the main body 300 to the second opening 210. In some embodiments, the continuous outer wall is shaped and sized so as to be capable of being inserted into a mouth of a rescuer. In some such embodiments, the continuous outer wall is generally cylindrical.

In some embodiments, the continuous outer wall defines a fourth diameter adjacent to the second opening 210. In some such embodiments, the fourth diameter is approximately between one and one and a half inches. In other such embodiments, the fourth diameter is approximately equivalent to the second diameter defined by the first tube 100.

In some embodiments, a longitudinal axis of the second tube 200 extends from the second opening 210 to the interior area 320 of the main body 300. In some such embodiments, a cross section of the second passageway 220 adjacent to the second opening 210 and perpendicular to the longitudinal axis of the second tube 200 defines a fourth area. In some such embodiments, the fourth area is approximately equivalent to the second area associated with the cross section of the first passageway.

In some embodiments, the main body 300 is sized and shaped so as to enable a rescuer to securely hold the extraction device 10 while using the extraction device 10 to remove a foreign object from the choking victim's windpipe. In some embodiments, the main body 300 is generally in the shape of a disk defining a third diameter. In some such embodiments, the third diameter is larger than the second diameter defined by the first tube 100. For instance, in some embodiments, the third diameter is approximately between three and four inches.

In a preferred embodiment, the present invention includes a filter 20 positioned between the first 110 and second 210 openings. In this way, objects entering the first passageway 120 through the first opening 110 are prevented from exiting the second opening 210 through the second passageway 220, thereby preventing the objects from becoming caught in the rescuer's throat.

In some embodiments, the filter 20 is positioned within the interior area 320 of the main body 300. In some such embodiments, the interior area 320 defines a third area that is larger than the first area associated with the cross section of the first passageway 120. In some such embodiments, the third area is at least twice as large as the first area. In other such embodiments, the third area is at least five times as large as the first area. In still other such embodiments, each of the first and third areas are circular in shape with the first area having approximately a one-inch diameter and the third area having approximately a three-inch diameter.

The present invention also pertains to a method of removing a foreign object from a choking victim's windpipe. In a preferred embodiment, the method includes plugging the victim's nose. In this way, air is inhibited, and maybe even prevented, from passing through the victim's nasal passage. In other embodiments, the method includes inserting a first end of an extraction device 10 into the victim's mouth such that a first passageway 120 of a first tube 100 of the extraction device 10 is in fluid communication with the victim's windpipe through a first opening 110 of the first tube 100. In other embodiments, the extraction device is in fluid communication with the mouth and depresses the victim's tongue. In some embodiments, the method further includes creating a low-pressure environment within an interior area 320 of the extraction device 10. In some such embodiments, the first passageway 120 extends between the first opening 110 and the interior area 320 of the extraction device 10 such that air in the victim's mouth is drawn towards the interior area 320 of the extraction device 10, thereby creating a low-pressure environment within the victim's mouth so as to assist in dislodging the foreign object from the victim's windpipe. In some embodiments, the method further includes holding the victim's cheeks, lips, and/or chin as to create a seal around the first tube with the victim's lips.

In a preferred embodiment, the low-pressure environment is created by the rescuer. In some embodiments, the method includes inserting a second end of the extraction device 10 into the rescuer's mouth such that a second passageway 220 of a second tube 200 of the extraction device 10 is in fluid communication with the rescuer's mouth through a second opening 210 of the second tube 200. In some embodiments, the method further includes sucking on the second end of the extraction device 10 by the rescuer so as to create the low-pressure environment within the interior area 320 of the extraction device 10. In this way, the rescuer is able to quickly and easily control the amount of suction the victim is exposed to.

The present invention is also directed to a rescue kit for use by a rescuer on a choking victim. In a preferred embodiment, the rescue kit includes a nose plug and an extraction device 10. In some embodiments, the rescue kit further includes instructions for performing one or more various method of the present invention.

In some embodiments, the longitudinal axis of the first tube 100 is collinear with the longitudinal axis of the second tube 200. In other embodiments, the longitudinal axis of the first tube 100 is collinear with a center axis of the main body 300. In still other embodiments, the longitudinal axis of the first tube 100 is coincident with a center point of the filter 20.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A method of removing a foreign object from a choking victim's windpipe, the method comprising:
    inserting a first end of an extraction device into the victim's mouth, wherein the extraction device comprises a first passageway extending between said first end and an interior area of the extraction device;
    inserting a second end of the extraction device into a rescuer's mouth, wherein the extraction device comprises a second passageway extending between the second end and said interior area; and
    creating a low-pressure environment within said interior area of the extraction device by drawing air into said rescuer's mouth, so as to draw air from the victim's mouth, thereby creating a low-pressure environment within the victim's mouth, thereby assisting in dislodging the foreign object from the victim's windpipe,
    wherein the first end defines an opening in communication with the first passageway, the opening being configured to receive the foreign object after the foreign object is dislodged from the victim's windpipe, thereby removing the foreign object from the victim's mouth so as to ensure that the foreign object will not migrate back into the victim's windpipe,
    wherein said interior area comprises a filter with a surface area at least two times larger than a cross-sectional area of the opening of said first end, and
    wherein the opening of the first end of the extraction device is displaced from the foreign object when the foreign object is lodged in the victim's windpipe.

2. The method of claim 1, further comprising:
    plugging the victim's nose so as to inhibit air from passing through the victim's nasal passageway.

3. The method of claim 1, further comprising:
    holding the victim's lips around the first end of the extraction device so as to create a seal around the first end of the extraction device.

4. The method of claim 1, wherein:
    said filter is positioned between the first and second ends so as to prevent the foreign object from becoming caught in the rescuer's windpipe.

* * * * *